US008093556B2

(12) United States Patent
Zeile

(10) Patent No.: US 8,093,556 B2
(45) Date of Patent: Jan. 10, 2012

(54) DEVICE AND METHOD FOR ANALYZING A SAMPLE

(75) Inventor: Ulrike Zeile, Heidenheim (DE)

(73) Assignee: Carl Zeiss NTS GmbH, Oberkochen (DE)

( * ) Notice: Subject to any disclaimer, the term of this patent is extended or adjusted under 35 U.S.C. 154(b) by 290 days.

(21) Appl. No.: 12/584,283

(22) Filed: Sep. 2, 2009

(65) Prior Publication Data

US 2010/0059672 A1 Mar. 11, 2010

(30) Foreign Application Priority Data

Sep. 4, 2008 (DE) .......................... 10 2008 041 815

(51) Int. Cl.
 *H01J 37/244* (2006.01)
(52) U.S. Cl. .................... 250/306; 250/307; 250/309
(58) Field of Classification Search .................. 250/306, 250/307, 309, 310, 492.21
 See application file for complete search history.

(56) References Cited

U.S. PATENT DOCUMENTS

| 5,035,787 A | 7/1991 | Parker et al. |
| 5,986,264 A | 11/1999 | Grunewald |
| 6,303,932 B1 * | 10/2001 | Hamamura et al. ............ 850/43 |
| 6,835,931 B2 | 12/2004 | Wright et al. |
| 6,882,739 B2 | 4/2005 | Kurtz et al. |
| 2003/0012334 A1 | 1/2003 | Kurtz et al. |
| 2004/0011958 A1 | 1/2004 | Wright et al. |
| 2004/0108458 A1 | 6/2004 | Gerlach et al. |
| 2006/0219953 A1 | 10/2006 | Carleson |
| 2006/0274931 A1 | 12/2006 | Svidenko et al. |

FOREIGN PATENT DOCUMENTS

| DE | 196 08 082 A1 | 10/1996 |
| DE | 603 08 482 T2 | 6/2007 |
| EP | 1 473 560 A1 | 11/2004 |
| EP | 1 501 115 A2 | 1/2005 |
| EP | 1 577 927 A2 | 9/2005 |
| EP | 1 956 634 A1 | 8/2008 |
| GB | 2 225 156 A | 5/1990 |
| WO | WO88/09049 | 11/1988 |
| WO | WO2004/027684 A2 | 4/2004 |

* cited by examiner

*Primary Examiner* — Kiet Nguyen
(74) *Attorney, Agent, or Firm* — Muirhead and Saturnelli, LLC

(57) ABSTRACT

A device and method for analyzing a sample, in particular a sample which contains low-density materials, is provided. Ions of a predefined mass and/or a predefined elementary charge are selected from a plurality of ions. The selected ions are directed onto the sample for sample preparation. An electron beam is then directed onto the prepared sample and a spatial distribution of scattered electrons is measured.

20 Claims, 6 Drawing Sheets

DEVICE AND METHOD FOR ANALYZING A SAMPLE

TECHNICAL FIELD

This application relates to a device and method for analyzing a sample, in particular a sample which contains low-density materials.

BACKGROUND OF THE INVENTION

The use of an ion beam column for repairing semiconductor masks is known from the prior art. The ion beam column has an ion source, which provides a plurality of ions of different suitable elements, which have different ion masses. The ions are combined in an ion beam and directed toward a semiconductor mask to be repaired. A desired type of ions is selected on the basis of their mass with the help of a filter which provides both an electric field and a magnetic field. Ultimately only these selected ions are focused on the semiconductor mask as an ion beam. Due to an interaction of the ion beam incident on the semiconductor mask with the material of the semiconductor mask, interaction particles are generated, in particular secondary electrons or secondary ions, which are emitted from the semiconductor mask. A detector detects the interaction particles. Reference is made to U.S. Pat. No. 5,035,787 and WO 88/09049 regarding the above prior art, which are both incorporated herein by reference.

As mentioned previously, the known method relates to the repair of semiconductor masks only, however, not to an analysis of a sample.

For analyzing a crystalline structure of a sample it is known from the prior art to determine the distribution of electrons, which are backscattered from the sample after an electron beam has hit a sample. The above method is known by the designation EBSD (Electron Backscattered Diffraction). The use of the above method in a particle beam device which provides both an ion beam and an electron beam is known. A sample to be analyzed is initially prepared with the aid of the ion beam. Subsequently an electron beam is focused onto the sample. Due to the interaction between the electrons of the electron beam and the material of the sample, electrons are backscattered from the surface of the sample. The distribution of the backscattered electrons is determined to thereby obtain information about the crystalline structure of the sample. A two-dimensional detector in the form of a CCD camera may be used for determining the distribution of the backscattered electrons.

For samples containing low-density materials, which are examined in the above-mentioned particle beam device, however, no meaningful measurements are obtainable. The use of images of the spatial distribution of the backscattered electrons, generated by the EBSD method, provides no clear information about the crystalline structure of the above-mentioned sample. The conclusion has been drawn that this is probably due to the type of preparation of the sample. Gallium ions, which penetrate the sample and destroy the crystalline structure of the sample, are normally used for preparing the sample.

Accordingly, it would be desirable to provide a device and method for analyzing a sample with the help of which clear conclusions may be drawn about the crystalline structure even for samples composed of low-density materials.

SUMMARY OF THE INVENTION

According to the system described herein, a method for analyzing a sample includes initially generating first ions and second ions. The first ions and the second ions may be ionized atoms or ionized molecules. The first ions may have a first predefinable mass and/or a first predefinable number of elementary charges, while the second ions may have a second predefinable mass and/or a second number of elementary charges. The second predefinable mass may be different from the first predefinable mass. Alternatively or additionally, the second predefinable number of elementary charges may be different from the first predefinable number of elementary charges. An ion beam may be generated from the first ions and the second ions. Subsequently, the first ions or the second ions may be selected in the ion beam. The selected first ions or the selected second ions may be directed to the sample. In other words, only the selected ions, either the first ions or the second ions, remain in the ion beam which is directed to the sample. The non-selected ion type (i.e., the other of the first ions or the second ions) may be extracted from the ion beam and not directed to the sample. At least a portion of the sample may be prepared with the help of the selected first ions or the selected second ions directed to the sample. For example, the surface of the sample may be polished with the help of the selected first ions or the selected second ions. It is also provided in the method according to the system described herein that an electron beam may be generated and directed onto the prepared portion of the sample. The electrons of the electron beam interact with the sample; in particular, electrons are scattered from the surface of the sample. For example, these electrons may be backscattered from the sample. In other words, these electrons are scattered away from the surface of the sample, i.e., in the forward direction viewed from the surface. The scattered electrons which have a spatial distribution may be detected. The spatial distribution of the scattered electrodes may then be analyzed.

The system described herein is based on the consideration that, depending on the material of the sample, an ion type may be determined which allows sufficient preparation of the sample while not damaging the sample in a way that would prevent the adequate analysis of spatial distribution of the scattered electrons. In particular, it is provided according to the system described herein to use relatively heavy or highly charged ions because these normally do not penetrate a sample and damage it due to their size and charge. A variety of ions of different masses and/or numbers of elementary charges may be generated. Using a selection process, ions of a well-defined mass and/or a well-defined number of elementary charges may be selected and focused, onto the sample to be examined. A filter which provides both an electric field and a magnetic field (Wien filter) may be used, for example, for selecting the first ions or the second ions.

In an embodiment of the method according to the system described herein, it is provided that the first ions and/or the second ions are or contain at least one of the following elements: silicon (Si), chromium (Cr), iron (Fe), cobalt (Co), nickel (Ni), germanium (Ge), indium (In), tin (Sn), gold (Au), silver (Ag), lead (Pb), bismuth (Bi), neodymium (Nd), cesium (Cs), and arsenic (As). The ions are ionized atoms or ionized molecules (for example, $AuSi^+$ or $AuSi^{2+}$). In yet another embodiment it is provided that a variety of ions (ionized atoms or ionized molecules) of different elements may be generated, for example, of at least two or at least three of the above-mentioned elements. A "mixture" of different ions may thus be generated, which are then selected on the basis of their ion mass as explained above.

Alternatively or additionally, it is provided that the first ions and/or the second ions may contain a type of ions whose mass is greater than the mass of gallium. The use of gallium may be disadvantageous in some applications. Due to its relatively small mass, gallium has the characteristic of penetrating deep into a sample. In the case of some samples, this may result in the samples being damaged due to the deep penetration of gallium. Therefore, in these applications it is advantageous to select a type of ion whose mass is greater than the mass of gallium.

Furthermore, in another embodiment it is provided that the first ions and/or the second ions may have a mass greater than 100 atomic mass units. The conclusion has been drawn that ions of this type are particularly well-suited for the method according to the system described herein.

In another embodiment of the method according to the system described herein, the sample has a predefinable material. First ions and/or second ions which have low chemical and/or low physico-chemical affinity to the material of the sample are then selected. This ensures that the sample is not damaged by the selected first ions or the selected second ions.

In a further embodiment, it is provided that the sample to be analyzed may contain Al, Mg, or alloys of Al and/or Mg. The method according to the system described herein may be used, for example, with samples composed of low-density materials.

In a further embodiment, the method according to the system described herein may be combined with other measuring methods. In particular, it is provided that, when the electron beam hits the sample, cathodoluminescence light exiting the sample may be additionally detected. Alternatively or additionally, the sample may be examined using energy-dispersive X-ray spectroscopy (EDX), and/or the sample may be examined using wavelength-dispersive X-ray spectroscopy (WDX). Another embodiment provides that, additionally or alternatively to the above-mentioned measuring methods, the sample may be examined using secondary ion mass spectrometry (SIMS). Moreover, it is alternatively or additionally provided that the sample may be examined with the aid of an analysis of secondary electrons (i.e., electrons emitted by the sample, also known by the abbreviation SE) and/or of electrons backscattered from the sample (backscattered electrons, also known by the abbreviation BSE). The combination of at least one of the above-mentioned measuring methods with the method according to the system described herein is advantageous because it allows ascertainment of further characteristics of the sample to be analyzed.

In a further embodiment of the method according to the system described herein, the ion beam may be focused onto the sample. This takes place, for example, by using a suitable ion beam column. This makes it possible to perform an analysis of the composition of the sample at well-defined locations. It is provided in particular to initially prepare, with the aid of the ion beam, the surface of a sample to be examined. In this preparation, material is removed from the sample to be examined in particular and/or the sample to be examined is polished. This may be monitored, for example, via imaging, which is produced by the electron beam incident on the sample to be examined. Only after the preparation of the sample has been completed is the spatial distribution of the electrons scattered from the sample determined by detecting the scattered electrons.

In a further embodiment of the method according to the system described herein, it is provided that prior to the initial preparation, a spatial distribution of the electrons scattered from the sample is determined by detecting the scattered electrons. The preparation only takes place thereafter, as described above. Subsequently thereto, the spatial distribution of the electrons scattered from the sample may be determined again.

According to another embodiment of the method according to the system described herein, it is also provided that the method may be carried out multiple times consecutively in order to thus ascertain different data sets of the sample. For example, the steps of the above-mentioned preparation and the determination of the distribution of the scattered electrons are performed multiple times consecutively. In this way, it is possible to obtain a data set regarding the spatial distribution of the scattered electrons for each plane of the sample produced during the preparation. The individual data sets are then combined to form a three-dimensional data set of the sample. To determine the data set of a plane, it is provided in this embodiment that, after the preparation step, the spatial distribution of the scattered electrons is determined at different locations of the plane. For example, the spatial distribution at at least one first location of the sample is initially determined. Information about the first location and the spatial distribution of the scattered electrons determined at the first location are stored as a first data set. The spatial distribution of the scattered electrons is then determined at at least one second location of the sample. Information about the second location and the spatial distribution of the scattered electrons determined at the second location are stored as a second data set. By ascertaining a plurality of the above-mentioned data sets, it is possible to obtain a two-dimensional data set about the plane produced during the preparation.

In a further embodiment of the method according to the system described herein, it is provided that the scattered electrons may be detected with the aid of a scintillation detector which has a location-sensitive scintillation surface. In this way, it is possible to determine the spatial distribution of the electrons in a particularly precise manner.

In yet another embodiment of the method according to the system described herein, an image of the spatial distribution of the scattered electrons may be generated and displayed. Furthermore, it is provided, for example, to determine a crystalline structure of at least one crystallite of the sample and a spatial orientation of the crystallite in the sample with the aid of the spatial distribution of the scattered electrons. It is also provided to determine the spatial distribution of all crystallites and the spatial orientation of the crystallites. In a further embodiment, it is provided to display a result of the detection of the cathodoluminescence light and/or of X-rays and/or of secondary ions and/or of secondary electrons and/or of backscattered electrons to be able to draw further conclusions about the sample.

The system described herein also relates to a particle beam device for carrying out a method for analyzing a sample having one or more of the above-mentioned features. The particle beam device may have at least one ion generator that generates first ions and second ions, the first ions having a first predefinable mass and/or a first predefinable number of elementary charges, and the second ions having a second predefinable mass and/or a second predefinable number of elementary charges. The second predefinable mass may be different from the first predefinable mass. Alternatively or additionally, the second predefinable number of elementary charges may be different from the first predefinable number of elementary charges. Furthermore, the particle beam device may have at least one ion beam generator that generates an ion beam made up of the first ions and the second ions and at least one ion selector that selects the first ions or the second ions from the ion beam. Moreover, the particle beam device may be provided with at least one ion director that directs the selected first ions or the selected second ions to a sample, at least part of the sample being prepared with the aid of the selected first ions or the selected second ions. Furthermore, at least one electron beam generator that generates an electron beam, at least one electron beam director that directs the electron beam to the prepared portion of the sample, at least one detector that detects the electrons scattered from the sample which are spatially distributed, and at least one analyzer that analyzes the spatial distribution of the scattered electrons may be provided.

BRIEF DESCRIPTION OF THE DRAWINGS

Embodiments of the system described herein are explained below in greater detail with the aid of the figures, which are briefly described as follows.

DETAILED DESCRIPTION OF VARIOUS EMBODIMENTS

Figure 1:
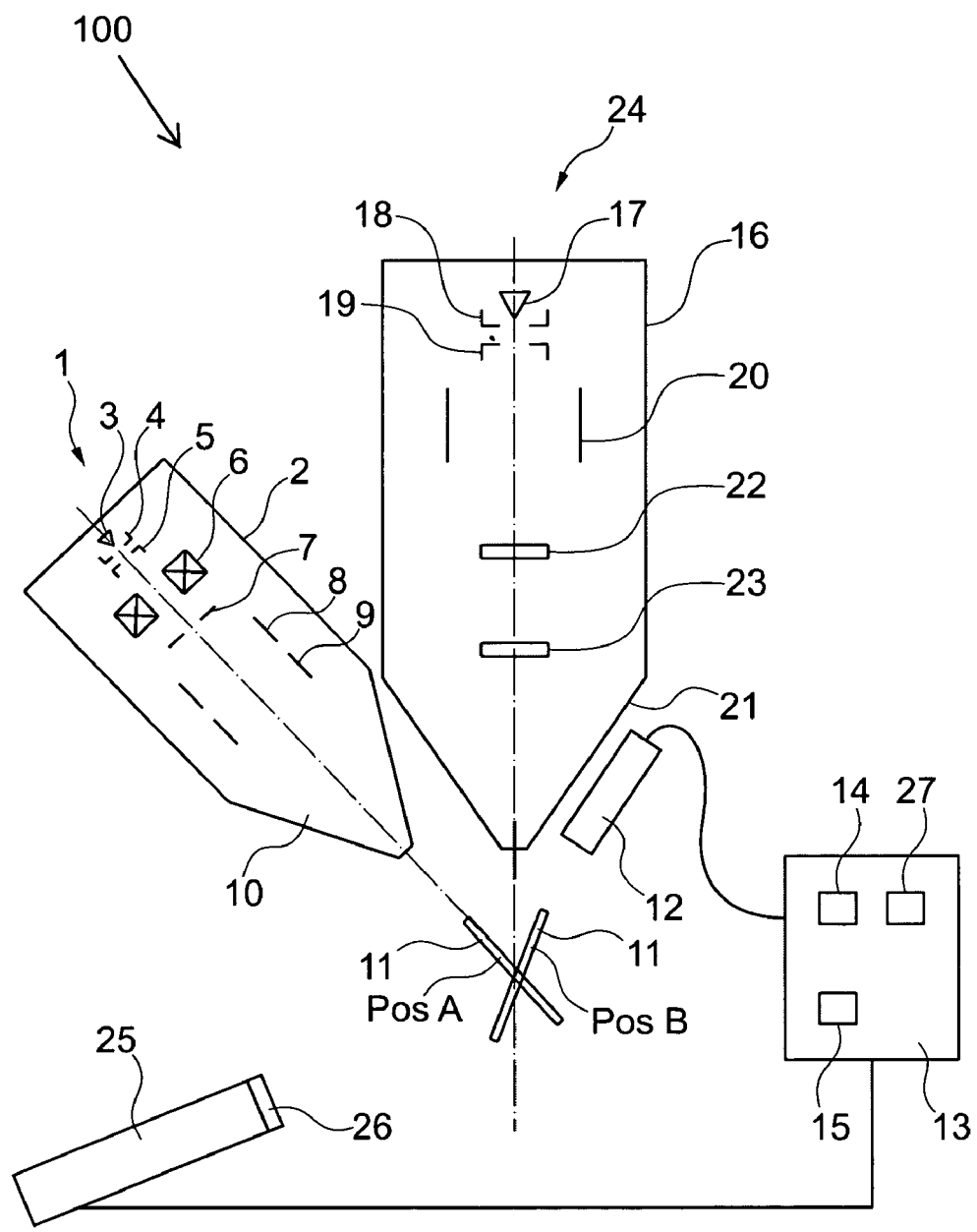
FIG. 1 shows a schematic representation of a particle beam device for carrying out a method for analyzing a sample according to an embodiment of the system described herein.

FIG. 1 shows a schematic representation of a particle beam device 100 which has an ion beam device 1 and an electron beam device 24 according to an embodiment of the system described herein. The method according to the system described herein, which is discussed in greater detail elsewhere herein, may be carried out using the described and illustrated particle beam device 100.

The ion beam device 1 may have an ion beam column 2 in which numerous units of the ion beam device 1 may be situated. In particular, an ion source 3 may be situated in the ion beam column 2. The ion source 3 may generate ions which form an ion beam in the ion beam column 2. The ion source 3 may generate a variety of ions of different masses and/or numbers of elementary charges. In the embodiment illustrated in FIG. 1, it is provided, for example, that the variety of ions has or contains ions of a plurality of the following elements: silicon (Si), chromium (Cr), iron (Fe), cobalt (Co), nickel (Ni), germanium (Ge), indium (In), tin (Sn), gold (Au), silver (Ag), lead (Pb), bismuth (Bi), neodymium (Nd), cesium (Cs), and arsenic (As). The ions may be ionized atoms or ionized molecules (for example, $AuSi^+$ or $AuSi^{2+}$). It is also provided, for example, that the variety of ions may contain ion types whose mass is greater than the mass of gallium. Furthermore, it is provided in particular that the variety of ions may have ions whose mass is greater than 100 atomic mass units, in accordance with the discussion noted elsewhere herein.

The variety of ions may be accelerated to a predefinable potential with the aid of an ion beam electrode 4 and then passed through a first condenser lens 5. A Wien filter 6 may be situated downstream from the first condenser lens 5. The Wien filter 6 may provide both an electric field and a magnetic field in such a way that ions having a well-defined mass and/or a well-defined number of elementary charges may be selected from the variety of ions that form the ion beam. Only these selected ions remain in the ion beam and are then directed toward a sample 11 to be examined. The non-selected ions may be therefore extracted from the ion beam.

The ion beam formed by the selected ions may be passed through an aperture 7 and then reach a first electrode system 8 and a second electrode system 9, which may be designed as scanning electrodes. The ion beam formed by the selected ions may be scanned over the sample 11 with the aid of the first electrode system 8 and the second electrode system 9. Beforehand, the ion beam may be focused onto the sample 11 with the aid of an objective lens 10. In this exemplary embodiment, the sample 11 is formed from Al, Mg, or alloys of Al and/or Mg. The surface of the sample 11 may be prepared with the aid of the ion beam directed to the sample 11, in particular, material may be removed to allow an examination with the aid of an EBSD method. This is discussed in greater detail elsewhere herein.

The electron beam device 24 may be a scanning electron microscope. The electron beam device 24 may have an electron column 16, in which units of the electron beam device 24 are situated.

Thus, an electron source 17 may be provided which generates electrons which are extracted with the aid of a first electrode 18. The electrons may be accelerated to a predefinable potential with the aid of a second electrode 19. The electrons are then passed through a second condenser lens 20, whereby an electron beam is formed, which, with the aid of an objective lens 21, is focused onto the sample 11 to be analyzed. Scanning electrodes (not illustrated) situated on the objective lens 21 may ensure that the electron beam can be scanned over the sample 11. When the electron beam hits the sample 11, interaction particles may be formed, in particular secondary electrons and backscattered electrons, which may be detected with the aid of a first detector 22 and a second detector 23 and used for imaging. It is thus possible to image the surface of the sample 11.

Furthermore, the particle beam device 100 may have a scintillation detector 25, which is provided with a location-sensitive scintillation surface 26. The scintillation detector 25 may be used for carrying out the EBSD method and detect electrons which, when the electron beam hits the sample 11, are backscattered from the surface of the sample 11. With the aid of the location-sensitive scintillation surface 26, the spatial distribution of the electrons backscattered from the surface of the sample 11 may be determined. For this purpose, the scintillation detector 25 may be connected to a control unit 13 which has a processor 15. The processor 15 may determine the spatial distribution and supply appropriate signals to a display device 27, with the aid of which the spatial distribution of the scattered electrons is made visible. The spatial distribution of the crystallites and the spatial orientation of the crystallites are thus determined.

In the exemplary embodiment described herein, two sample positions are provided, namely a first sample position A and a second sample position B. These are schematically illustrated in FIG. 1 and are discussed again in greater detail below.

Figure 2:
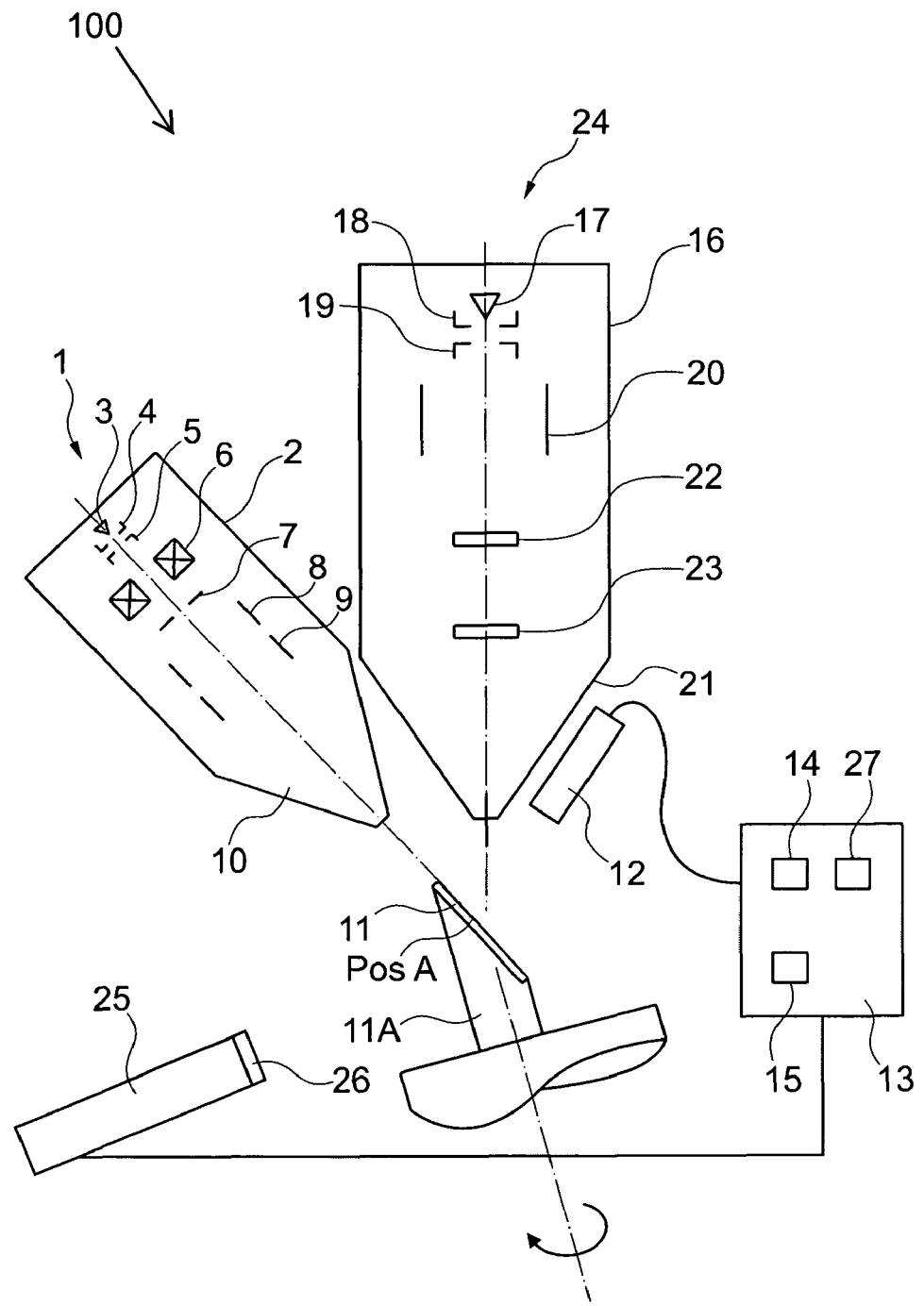
FIG. 2 shows another schematic representation of the particle beam device of FIG. 1.

FIG. 2 shows a representation of the particle beam device 100 of FIG. 1, in which the sample 11 is situated in the first sample position A. The sample 11 may be transferrable into the first sample position A with the aid of a movable sample holder 11A. In the first sample position A, the ion beam of the selected ions hits the sample 11 essentially in parallel and makes it possible to prepare the sample 11 by removing material from and polishing the sample 11 along the surface of the sample 11, which in FIG. 2 is oriented parallel to the ion beam. The preparation of the sample 11 may be observable with the aid of an image which is generated by the electron beam.

Figure 3:
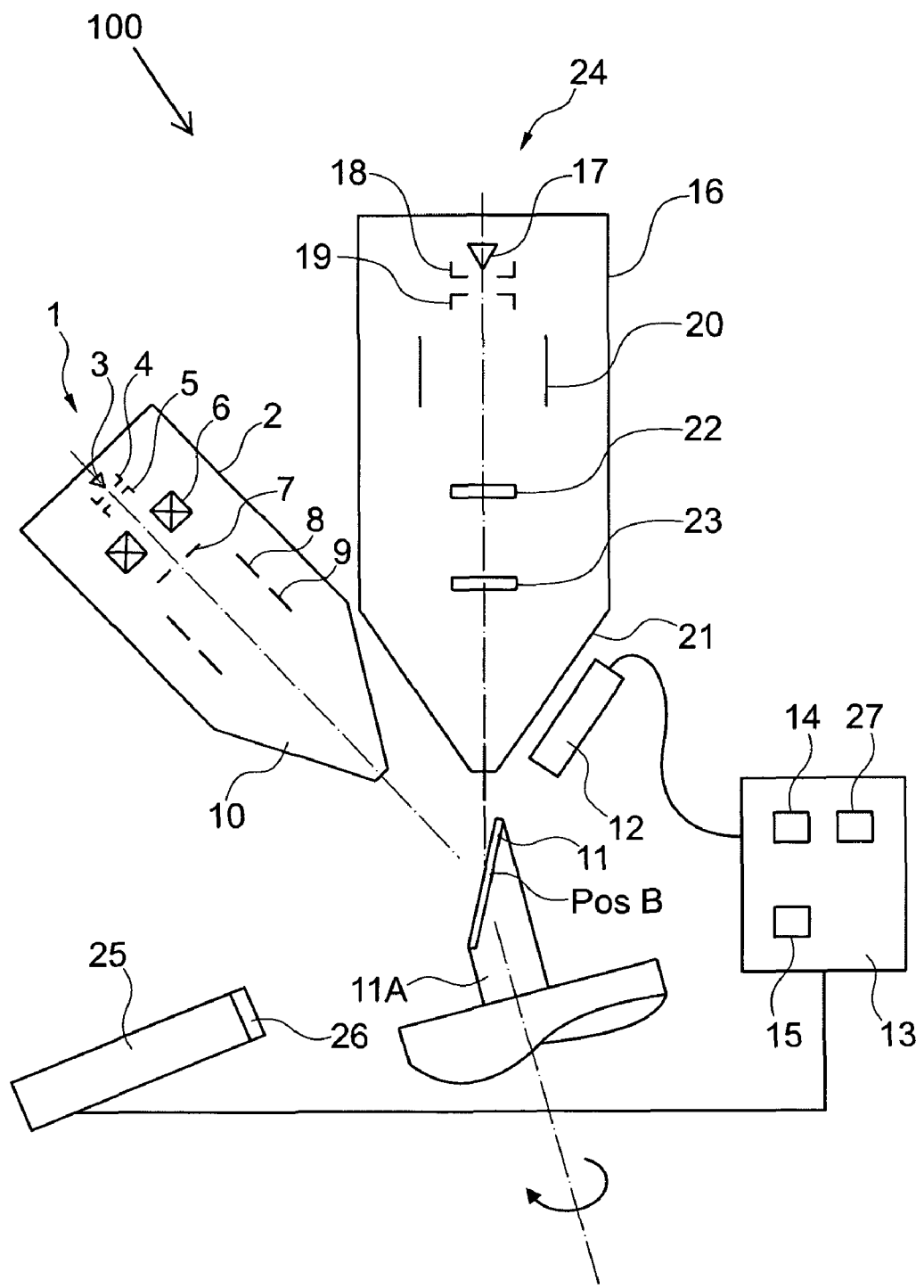
FIG. 3 shows yet another schematic representation of the particle beam device of FIG. 1.

FIG. 3 shows another representation of the particle beam device 100 of FIG. 1, in which the sample 11 is situated in the second sample position B. The sample 11 may be transferrable into the first or second sample position A or B by simply rotating the sample holder 11A about its rotation axis illustrated in FIGS. 2 and 3. No further movement of the sample holder 11A may be necessary. Instead, rotation about the rotation axis may be sufficient for changing positions. In the second sample position B, the surface of the sample 11 may be tilted with respect to the vertical. The spatial distribution of the backscattered electrons may be determined in this position, as will be discussed in greater detail below.

Figure 4:
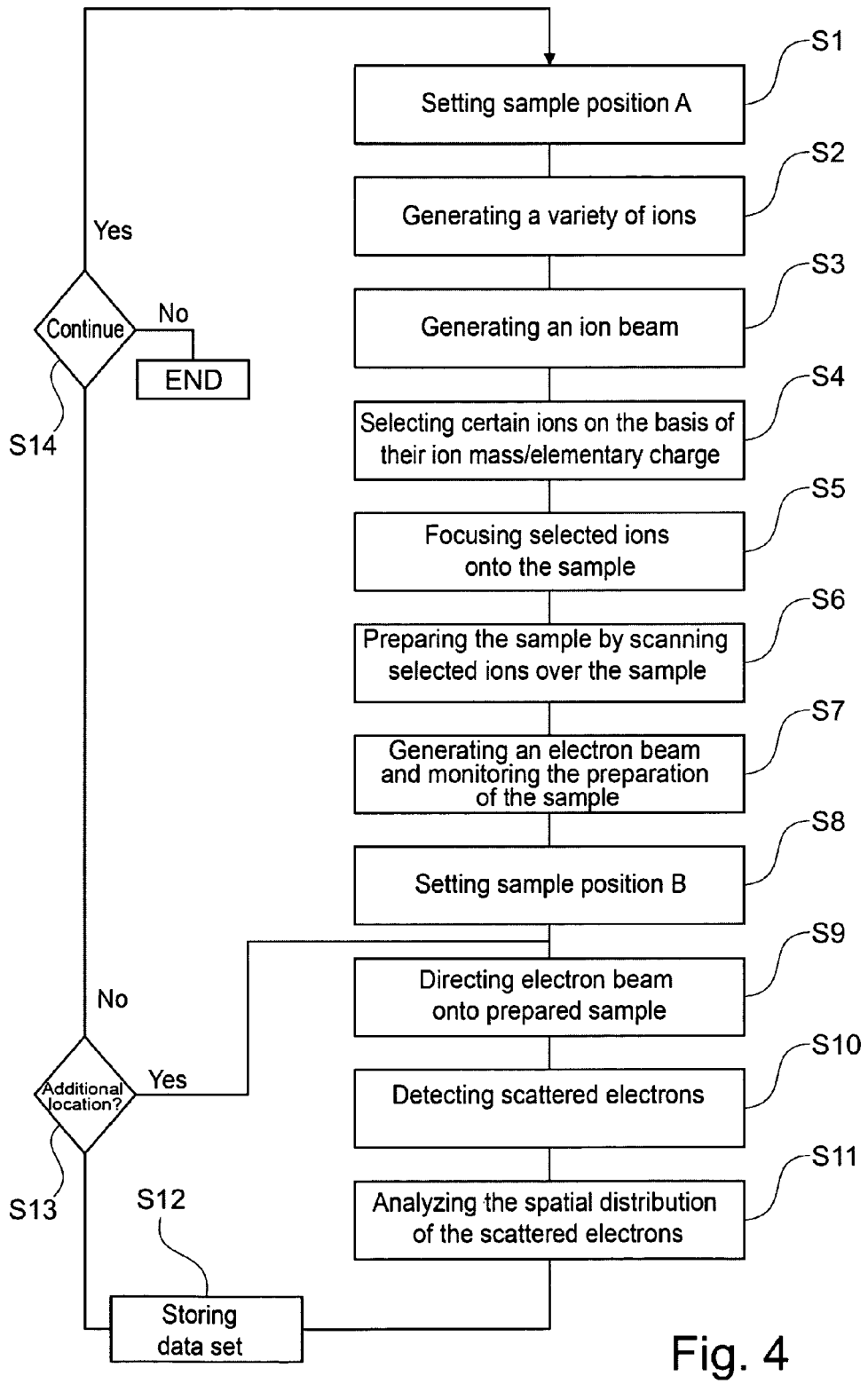
FIG. 4 shows a flow chart of an exemplary embodiment of a method according to the system described herein.

FIG. 4 shows a flow chart of an embodiment of the method according to the system described herein, which is carried out using the above-described particle beam device 100. The sample 11 to be analyzed is initially transported into the first sample position A illustrated in FIG. 2 (method step S1), in which the surface of the sample 11 is prepared. For this purpose, the variety of ions of different masses and/or different numbers of elementary charges may be initially generated (method step S2) as has been described above. Subsequently, an ion beam may be formed (method step S3) from the generated ions. With the help of the Wien filter 6, ions of a well-defined mass and/or a well-defined number of elementary charges may now be selected (method step S4). Only these selected ions remain in the ion beam and are then directed toward the sample 11. The non-selected ions may thus be extracted from the ion beam. The selected ions may be determined depending on the material of the sample 11. A type of ion may be selected which allows sufficient preparation of the sample 11, while the sample 11 is not damaged in such a way that examination with the aid of EBSD is no longer possible. In particular, ions are selected which have low chemical and/or low physico-chemical affinity to the material of the sample 11 and do not penetrate deep into the material of the sample 11.

In a further method step S5, the selected ions are now focused onto the sample 11 and scanned over the surface of the sample 11. The surface of the sample 11 is thus prepared (method step S6). The preparation may be observable by imaging the surface of the sample 11. For this purpose, an electron beam may be generated, using which images of the surface of the sample 11 may be generated as mentioned previously (method step S7).

After the preparation of the sample 11, the sample 11 may be transported into the second sample position B (method step S8), which is illustrated in greater detail in FIG. 3. In this position, the electron beam is focused onto the prepared sample 11 at a predefinable point (location) on the sample 11, whereby interactions take place between the electrons of the electron beam and the sample 11 at the predefinable location. Electrons are backscattered from the sample 11. These backscattered electrons are detected with the aid of scintillation detector 25 (method step S10). Finally, the spatial distribution of the backscattered electrons may be determined (method step S11). This may be done with the aid of the above-mentioned control unit 13. The spatial distribution of the detected electrons may be displayed on the display device 27.

In order to obtain information about a single plane of the sample 11 prepared by the ion beam and to make two-dimensional representations of a single plane possible, it is provided in this embodiment that method steps S9 through S11 may be carried out multiple times consecutively, each for a different location on the sample 11. If the method is carried out multiple times consecutively, in a method step S12, information is stored about the location of the sample 11 onto which the ion beam or electron beam was focused, and about the distribution of backscattered electrons prevailing there. Subsequently a decision is made in a method step S13 of whether the method steps S9 through S11 are used for a further location on the already prepared sample 11. If the answer is "yes," the method steps S9 through S11 may be used for a further location, which, however, may be different from the previous location. In this way, a two-dimensional representation may be initially produced for a prepared plane of the sample 11. If it is established in the method step S13 that no further location is to be measured on the already prepared sample 11, a decision is made in a method step S14 of whether the method is to be continued. If the method is to be continued, the sample 11 may be further prepared by repeating the method steps S1 through S7. For example, an additional plane of the sample 11 may be exposed, which may then be measured with the aid of the method steps S8 through S11 at at least one location on the exposed additional plane. A three-dimensional representation of the sample 11 may then be calculated from the individual two-dimensional representations of the individual planes.

Using the above-described method, it is possible to determine and display in three dimensions the spatial distribution of all crystallites and the spatial orientation of all crystallites.

Figure 5:
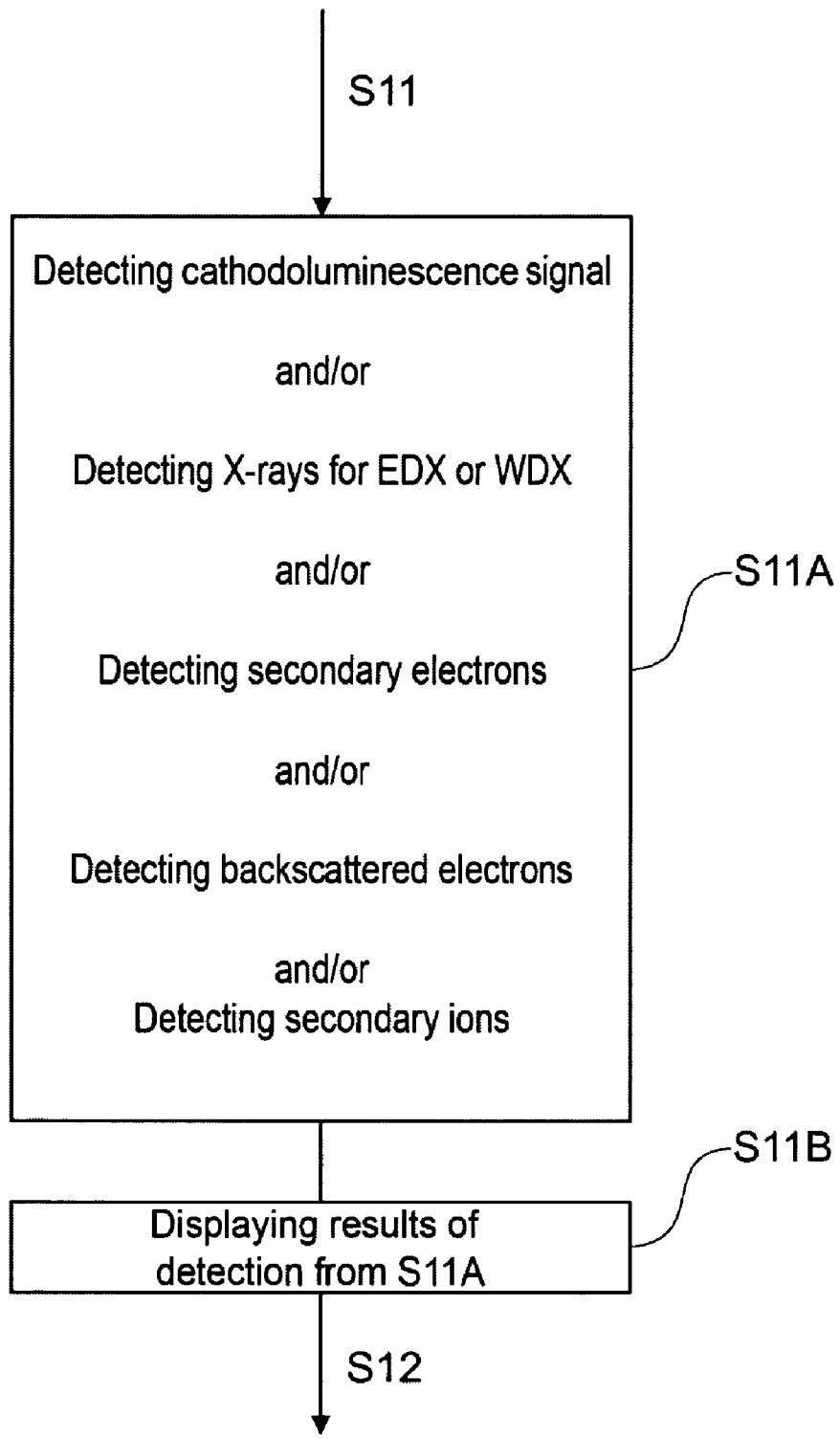
FIG. 5 shows further method steps of the method of FIG. 4.
Figure 6:
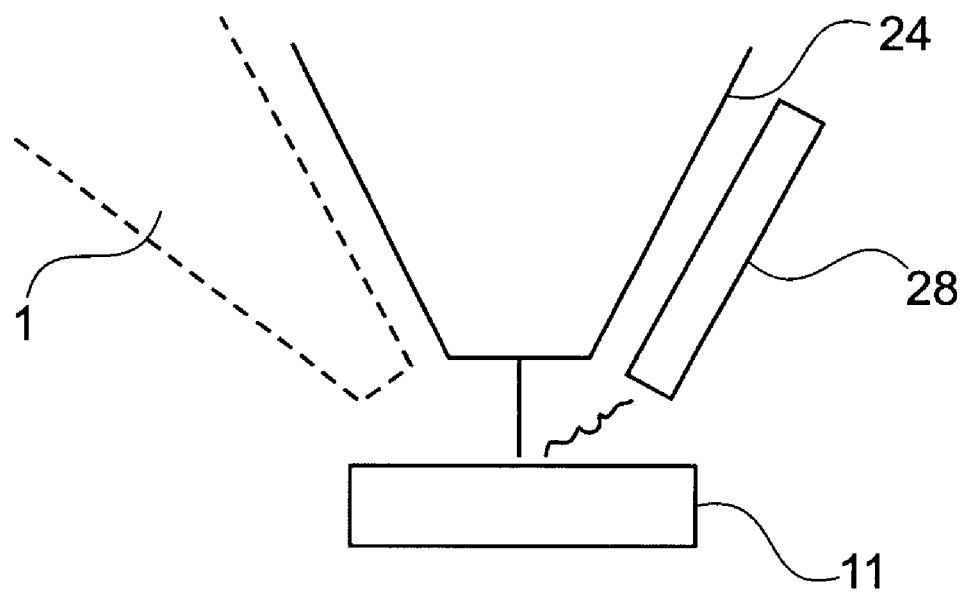
FIG. 6 shows a schematic representation of a particle beam device for carrying out a method having a detector situated above the sample according to an embodiment of the system described herein.

FIG. 5 shows a refinement of the method according to the system described herein according to FIG. 4. In this embodiment, an additional method step S11A may be introduced between method steps S11 and S12. In method step S11A, further methods may be carried out for examining the sample 11 at the location onto which the electron beam was focused in the method step S9. For example, it is provided that the cathodoluminescence light emitted by the sample 11 due to the incidence of the electron beam on the sample 11 may also be detected in order to obtain further information about the composition of the sample 11. This may be accomplished, for example, by using a third detector 28, which may be situated above the sample 11 in the direction of the electron beam device 24 (see FIG. 6). Additionally or alternatively, it is provided to detect X-ray beams in order to examine the sample 11 with the aid of energy-dispersive X-ray spectroscopy (EDX) and/or with the aid of wavelength-dispersive X-ray spectroscopy (WDX). This may also be accomplished with the aid of a detector which may be situated above the sample 11 in the direction of the ion beam device 1 (for example, in the proximity of the third detector 28). Again additionally or alternatively, it is provided for this purpose to detect secondary electrons and/or backscattered electrons. It is furthermore additionally or alternatively provided to detect secondary ions in order to examine the sample 11 with the aid of secondary ion mass spectrometry (SIMS). For this purpose, the sample 11 may be transported again into the first sample position A. When the ion beam hits the surface of the sample 11, secondary ions are generated, which may be examined using mass spectroscopy. An ion mass analyzer 12, which generates a mass spectrum, may be provided for this purpose. The generated mass spectrum may then be compared with a plurality of mass spectra which are stored in a memory unit 14 of the control unit 13. The generated mass spectrum may be compared with the stored mass spectra with the aid of the processor 15 of the control unit 13. In this way it is possible to determine the material of which the sample 11 is composed. Instead of the ion mass analyzer 12, another detector may also be situated at this point, which is capable of receiving interaction particles or interaction radiation from the sample 11 and forwarding them for analysis.

The method steps S10, S11, and S11A, or the individual or plurality of partial steps of method step S11A (i.e., the different detections), may be carried out consecutively or also simultaneously. The result of the different detections of the method step S11A may be displayed on the display device 27 (method step S11B).

Other embodiments of the invention will be apparent to those skilled in the art from a consideration of the specification or practice of the invention disclosed herein. It is intended that the specification and examples be considered as exemplary only, with the true scope and spirit of the invention being indicated by the following claim.

What is claimed is:

1. A method for analyzing a sample, comprising:
generating first ions and second ions, the first ions having at least one of: a first predefinable mass and a first predefinable number of elementary charges, and the second ions having at least one of: a second predefinable mass and a second predefinable number of elementary charges, wherein the first ions are different from the second ions according to at least one of: (i) the second predefinable mass being different from the first predefinable mass, and (ii) the second predefinable number of elementary charges being different from the first predefinable number of elementary charges;
generating an ion beam from the first ions and the second ions;
selecting, as selected ions, the first ions or the second ions in the ion beam;
directing the selected ions to the sample, at least a portion of the sample being prepared using the selected ions;
generating an electron beam;
directing the electron beam onto the prepared portion of the sample;
detecting spatially distributed electrons scattered from the sample; and
analyzing a spatial distribution of the scattered electrons.

2. The method as recited in claim 1, wherein backscattered electrons are detected.

3. The method as recited in claim 1, wherein at least one of: the first ions and the second ions are or contain at least one of the following elements: Si, Cr, Fe, Co, Ni, Ge, In, Sn, Au, Ag, Pb, Bi, Nd, Cs, and As.

4. The method as recited in claim 1, wherein at least one of: the first ions and the second ions include a type of ions whose mass is greater than that of gallium.

5. The method as recited in claim 1, wherein at least one of: the first ions and the second ions have a mass greater than 100 atomic mass units.

6. The method as recited in claim 1, wherein selecting the first ions or the second ions includes selecting the first ions or the second ions depending on at least one of: a chemical affinity and a physico-chemical affinity of the sample.

7. The method as recited in claim 1, wherein selecting the first ions or the second ions includes selecting the first ions or the second ions depending on at least one of: a chemical affinity and a physico-chemical affinity of the ions to the sample.

8. The method as recited in claim 1, wherein the sample includes a predefinable material, and wherein ions which have at least one of: a low chemical affinity and a low physico-chemical affinity to the predefinable material of the sample are selected as the selected ions.

9. The method as recited in claim 8, wherein the sample contains at least one of: Al, Mg, alloys of Al, and alloys of Mg.

10. The method as recited in claim 1, further comprising: detecting cathodoluminescence light exiting from the sample upon incidence of the electron beam.

11. The method as recited in claim 1, further comprising: examining the sample using at least one of: energy-dispersive X-ray spectroscopy; wavelength-dispersive X-ray spectroscopy; secondary ion mass spectrometry; and an analysis of at least one of: secondary electrons and backscattered electrons.

12. The method as recited in claim 1, wherein the ion beam is focused onto the sample.

13. The method as recited in claim 1, wherein the method is carried out at at least one first location of the sample, and information about the first location and about the spatial distribution of the scattered electrons prevailing at the first location is stored as a first data set, and wherein the method is carried out at at least one second location of the sample, and information about the second location and the spatial distribution of the scattered electrons prevailing at the second location is stored as a second data set.

14. The method as recited in claim 1, wherein the scattered electrons are detected with the aid of a scintillation detector which has a location-sensitive scintillation surface.

15. The method as recited in claim 1, wherein the first ions or the second ions are selected using a Wien filter.

16. The method as recited in claim 1, further comprising: generating and displaying an image of the spatial distribution of the scattered electrons.

17. The method as recited in claim 1, further comprising: displaying a result of detection of at least one of: cathodoluminescence light, X-rays, secondary ions, secondary electrons, and backscattered electrons.

18. The method as recited in claim 1, further comprising: determining a crystalline structure of at least one crystallite of the sample and a spatial orientation of the crystallite in the sample using the spatial distribution of the scattered electrons.

19. The method as recited in claim 1, wherein a spatial distribution of a plurality of crystallites and a spatial orientation of the plurality of crystallites in the sample are determined using the spatial distribution of the scattered electrons.

20. A particle beam device for analyzing a sample, comprising:
at least one ion generator that generates first ions and second ions, the first ions having at least one of: a first predefinable mass and a first predefinable number of elementary charges, and the second ions having at least one of: a second predefinable mass and a second predefinable number of elementary charges, wherein the first ions are different from the second ions according to at least one of: (i) the second predefinable mass being different from the first predefinable mass, and (ii) the second predefinable number of elementary charges being different from the first predefinable number of elementary charges;
at least one ion beam generator that generates an ion beam from the first ions and the second ions;
at least one ion selector that selects, as selected ions, the first ions or second ions in the ion beam;
at least one ion director that directs the selected ions to the sample, at least a portion of the sample being prepared using the selected ions;
at least one electron beam generator that generates an electron beam;
at least one electron beam director that directs the electron beam onto the prepared portion of the sample;
at least one detector that detects spatially distributed electrons scattered from the sample; and
at least one analyzer that analyzes a spatial distribution of the scattered electrons.

* * * * *